United States Patent [19]

Grosskinsky et al.

[11] Patent Number: 4,735,741

[45] Date of Patent: Apr. 5, 1988

[54] PREPARATION OF SOLUTIONS OF MOLECULAR OXYGEN IN LIQUID HYDROCARBONS

[75] Inventors: Otto-Alfred Grosskinsky, Ludwigshafen; Guenter Herrmann, Heidelberg; Ulrich Loeffler, Dannstadt-Schauernheim; Rolf Schnabel, Schifferstadt; Dieter Stuetzer, Ludwigshafen, all of Fed. Rep. of Germany

[73] Assignee: BASF Aktiengesellschaft, Ludwigshafen, Fed. Rep. of Germany

[21] Appl. No.: 854,917

[22] Filed: Apr. 23, 1986

[30] Foreign Application Priority Data

Apr. 25, 1985 [DE] Fed. Rep. of Germany ....... 3514924

[51] Int. Cl.$^4$ ........................ C07C 45/27; C07C 45/33

[52] U.S. Cl. ................................ 252/188.31; 568/357; 568/836

[58] Field of Search .................... 252/188.31; 568/836, 568/357; 423/579

[56] References Cited

U.S. PATENT DOCUMENTS

| | | | |
|---|---|---|---|
| 3,564,058 | 2/1971 | Lang et al. | 568/360 |
| 3,957,876 | 5/1976 | Rapoport et al. | 568/836 X |
| 4,587,363 | 5/1986 | Hartig et al. | 568/836 X |

*Primary Examiner*—John F. Terapane
*Assistant Examiner*—Virginia B. Caress
*Attorney, Agent, or Firm*—Keil & Weinkauf

[57] ABSTRACT

Solutions of molecular oxygen in liquid hydrocarbons are prepared by bringing a liquid hydrocarbon into contact with molecular oxygen under superatmospheric pressure in a vertical absorption zone, by a process in which (a) a layer of water is maintained at the lower end of the absorption zone, (b) molecular oxygen is passed into the layer of water, (c) a liquid hydrocarbon is fed in above the layer of water, (d) the finely divided molecular oxygen rising from the layer of water is passed upward together with the liquid hydrocarbon at from 0° to 50° C., with thorough mixing in the absorption zone, with the proviso that no cohesive gas phase is formed, and (e) the solution of molecular oxygen in the liquid hydrocarbon is discharged in the upper part of the absorption zone.

9 Claims, No Drawings

PREPARATION OF SOLUTIONS OF MOLECULAR OXYGEN IN LIQUID HYDROCARBONS

German Laid-Open Application DOS. No. 1,593,700 discloses a process in which molecular oxygen is dissolved in cyclohexane by feeding the latter to the top of an absorption column and passing molecular oxygen countercurrent to it.

In the presence of molecular oxygen, in contrast to air, hydrocarbons have the disadvantageous property of detonating. This applies in particular at elevated temperatures and when hydrocarbon films form on solid surfaces. Moreover, there is a danger that, when the oxygen feed is interrupted, hydrocarbons will penetrate into the oxygen line and detonate.

It is an object of the present invention to provide a method of dissolving molecular oxygen in liquid hydrocarbons so that there is no danger of denotation and no sources of danger arise even under exceptional operating conditions, for example a drop in pressure or failure of the oxygen feed.

We have found that this object is achieved by a process for the preparation of solutions of molecular oxygen in liquid hydrocarbons by bringing a liquid hydrocarbon into contact with molecular oxygen under superatmospheric pressure in a vertical absorption zone, wherein (a) a layer of water is maintained at the lower end of the absorption zone,
(b) molecular oxygen is passed into the layer of water,
(c) the liquid hydrocarbon is fed in above the water
(d) the finely divided molecular oxygen rising from the water layer is passed upward together with the liquid hydrocarbon at from 0° to 50° C., with thorough mixing in the absorption zone, with the proviso that no cohesive gas phase is formed, and
(e) the solution of molecular oxygen in the liquid hydrocarbon is discharged in the upper part of the absorption zone.

The novel process has the advantages that critical operating states are avoided and, in particular, no sources of danger arise even during exceptional operating conditions, such as failure of the oxygen feed.

According to the invention, the starting materials used are liquid hydrocarbons, in particular alkanes of 4 to 18 carbon atoms, cycloalkanes containing 5 to 10 carbon atoms in the ring, and alkylaromatics of 7 to 12 carbon atoms. Cycloalkanes having the stated number of carbon atoms, in particular cyclohexane, have become particularly important.

The molecular oxygen used advantageously contains less than 5, in particular less than 1, % by volume of an inert gas, such as nitrogen, carbon dioxide or a noble gas.

The dissolution process is carried out in a vertical absorption zone, for example an absorption tower, which advantageously has a length/diameter ratio of from 5:1 to 20:1.

A layer of water is maintained at the lower end of the absorption zone, this layer advantageously occupying from 10 to 50% of the volume of the absorption zone. The layer of water advantageoulsy contains salts, such as alkali metal salts, eg. sodium chloride, sodium sulfate or potassium phosphate. The salt content is preferably from 50 to 90% by weight, based on the saturation value. Moreover, it has proven useful for the layer of water additionally to contain surfactants, such as cationic, anionic or neutral surfactants. Examples of suitable surfactants are sulfates or phosphates of longchain alcohols.

In general, a content of from 0.001 to 0.1% by weight of surfactants is sufficient.

The molecular oxygen is advantageously passed in finely divided form into the layer of water.

The liquid hydrocarbon is fed into the absorption zone above the layer of water, advantageously directly above this layer.

The finely divided molecular oxygen rising from the layer of water is passed upward together with the liquid hydrocarbon, with thorough mixing in the absorption zone. Because the molecular oxygen is finely dispersed in the layer of water, buoyancy causes it to pass automatically into the hydrocarbon layer, where it is present in finely divided form. It should be ensured that no cohesive gas phase is formed. This is achieved if the absorption zone is always kept completely full of liquid and a small bleed stream, eg. from 0.005 to 0.1 times the total amount of hydrocarbon fed in, is removed, advantageously at the uppermost end, and stripped with nitrogen. This prevents the formation of a cohesive gas phase. The liquid hydrocarbon obtained in this procedure is added to the starting hydrocarbon. To achieve more thorough mixing, the absorption zone advantageously has, for example, from 1 to 6 constrictions along its length, in the part in which the liquid hydrocarbon is passed upward together with molecular oxygen. Advantageously, baffles are located between the constrictions. It is also possible for a plurality of constrictions to be arranged in one plane. The constrictions are advantageously in the form of nozzle openings so that the rising mixture of hydrocarbons and molecular oxygen reach a flow rate of from 2 to 60 m/s at the nozzle exit. It has also proven advantageous to circulate some of the solution of molecular oxygen in the hydrocarbon. Advantageously, the said solution is removed near the upper end of the absorption column in an amont which corresponds to 2–50 times the amount of hydrocarbon fed in, and is recycled to the absorption zone at a point directly above the layer of water.

The absorption is carried out at from 0° to 50° C. The temperature is chosen so that, as far as possible, it is only a few degrees above the melting point of the water or of the hydrocarbon, whichever of the two is the higher. Advantageously, the pressure is maintained at from 10 to 100 bar and care is taken to ensure that it corresponds in each case to 1.1–1.5 times the saturation pressure at the particular temperature used. The amount of oxygen dissolved in the hydrocarbons is advantageously such that a degree of saturation of from 60 to 90% is achieved under the particular pressure and temperature conditions used.

It has proven advantageous to compensate any pressure fluctuations by varying the amount of water in the water layer. For example, if there is a drop in pressure due to a leak, additional water is pumped into the absorption zone and the formation of a cohesive gas phase is thus avoided.

The solutions of molecular oxygen in liquid hydrocarbons, which are obtainable by the process of the invention, are useful for further reaction in the production of oxidation products; for example, cyclohexane solutions containing molecular oxygen are used for the preparation of cyclohexanone and cyclohexanol.

We claim:

1. A process for the preparation of a solution of molecular oxygen in a liquid hydrocarbon, wherein (a) a layer of water is maintained in the lower end of a vertical absorption zone, said water layer occupying from 10 to 50% of the volume of the absorption zone, (b) molecular oxygen is passed into the layer of water, (c) a liquid hydrocarbon is fed in above the layer of water, (d) the finely divided molecular oxygen rising from the layer of water is passed upward together with the liquid hydrocarbon under superatmospheric pressure at from 0 to 50 C, with thorough mixing in the absorption zone with the proviso that, the absorption zone is kept full of liquid, and (e) the solution of molecular oxygen in the liquid hydrocarbon is discharged in the upper part of the absorption zone.

2. The process of claim 1, wherein the solution of molecular oxygen in the hydrocarbon is circulated in an amount which is from 2 to 50 times the amount of hydrocarbon fed in.

3. The process of claim 1, wherein the mixture of the hydrocarbon and molecular oxygen is passed through constrictions along the absorption zone.

4. The process of claim 1, wherein the absorption is carried out under from 10 to 100 bar.

5. The process of claim 1, wherein the layer of water contains a salt.

6. The process of claim 1, wherein the layer of water contains a surfactant.

7. The process of claim 1, wherein the pressure in the absorption zone is regulated by the amount of water in the water layer.

8. The process of claim 1, wherein the degree of saturation of molecular oxygen in the liquid hydrocarbon is maintained at from 60 to 90%, depending on the particular temperature and pressure conditions used.

9. The process of claim 1, wherein a small amount of liquid is removed from the uppermost end of the absorption zone.

* * * * *